United States Patent [19]

Goel

[11] Patent Number: 4,628,102

[45] Date of Patent: Dec. 9, 1986

[54] NOVEL MONOMERS CONTAINING BICYCLIC AMIDE ACETAL AND EPOXY FUNCTIONAL GROUPS

[75] Inventor: Anil B. Goel, Worthington, Ohio

[73] Assignee: Ashland Oil, Inc., Ashland, Ky.

[21] Appl. No.: 766,361

[22] Filed: Aug. 16, 1985

[51] Int. Cl.$^4$ ............................................. C07D 498/00
[52] U.S. Cl. ..................................................... 548/218
[58] Field of Search ......................................... 548/218

[56] References Cited

PUBLICATIONS

"Bicyclic Amide Acetals, Synthesis and Reactions" Feinauer, Roland: *Synthesis:* International Journal of Methods in Organic Chemistry: No. 1, pp. 16-26 (1971).

*Primary Examiner*—Paul R. Michl
*Assistant Examiner*—Alex H. Walker
*Attorney, Agent, or Firm*—John F. Jones

[57] ABSTRACT

The reaction of oxazolines with diepoxide compounds to form novel monomers containing both bicyclic amide acetal and epoxy functional groups is described.

14 Claims, No Drawings

NOVEL MONOMERS CONTAINING BICYCLIC AMIDE ACETAL AND EPOXY FUNCTIONAL GROUPS

This invention relates to novel monomers containing both bicyclic amide acetal and epoxy functional groups and to a method for preparing them by reaction, of oxazolines with diepoxide compounds.

The synthesis of bicyclic amide acetals by the reaction of monoepoxide compounds with oxazolines is known in the prior art (SYNTHESIS, P. 16–26, 1971). The formation of monomers containing both bicyclic amide acetal and epoxy groups has not been disclosed heretofore.

The novel mixed bicyclic amide acetal and epoxy containing monomers embodied in this invention are materials from which a variety of polymers and copolymers can be made by the reaction of either or both of the bicyclic amide acetal and the epoxy functional groups.

The process by which the novel monomers of this invention are produced is illustrated by the following equation.

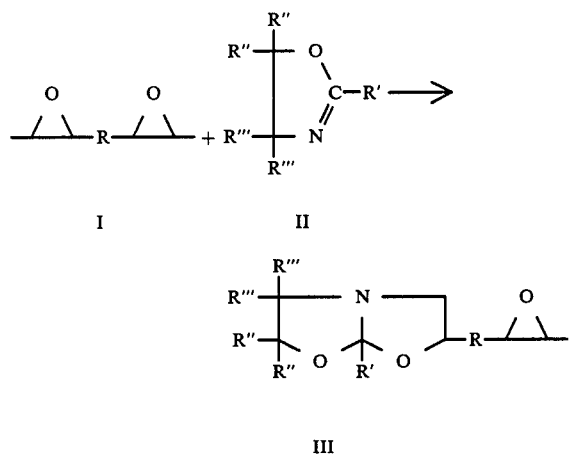

wherein R represents a linear or cyclic alkylene group having from 1 to 30 carbon atoms, an arylene group having from 6 to 12 carbon atoms, an alkylene ether group having from 1 to 20 carbon atoms, or an arylene ether group having from 6 to 12 carbon atoms; $R'$ represents an alkyl group having from 1 to 20 carbon atoms, an aryl group having from 6 to 12 carbon atoms or an alkaryl group having from 7 to 20 carbon atoms; $R''$ and $R'''$ independently represent hydrogen, an alkyl group having from 1 to 10 carbon atoms or an aryl group having from 6 to 12 carbon atoms.

The process of this invention is carried out in such stoichiometry that the reaction results primarily in product III formation. The epoxy to oxazoline equivalent ratios are preferably selected in the range of 5:1 to 1:1 and the more preferred ratio range is 2.5:1 to 1.5:1. The reaction temperature may be in the range of 120–200 degrees C. and preferably in the range of from 140–170 degrees C. Although the process can be carried out readily in the absence of any catalyst, catalysts such as alkali and alkaline earth metal salts, e.g., lithium chloride, may be used. Because the bicyclic amide acetal groups formed in the reaction are sensitive to moisture, the reaction is preferably carried out in a dry and inert atmosphere such as in a dry nitrogen atmosphere.

The novel monomers of this invention may be used in reactions with a variety of reactive substrates such as water to give products containing hydroxyl and epoxy groups. Because of the significant difference in the reactivities of the bicyclic amide acetal and epoxy groups, it is possible to carry out sequential reactions involving first one type of functional group and then the other. For instance, primary and secondary amines will react with epoxy groups under mild conditions whereas the amines will not react with the bicyclic amide acetal group under such conditions. Similarly, carboxylic acids will react with bicyclic amide acetal groups more readily and under milder conditions than they will react with epoxy groups.

The process and products of this invention are further illustrated in the following representative examples.

EXAMPLE 1

To a 100 ml three-neck round bottom flask equipped with a magnetic stirring bar, a thermometer with a temperature controller, a water condenser and a nitrogen gas inlet, was charged 25.7 g of 1,2,7,8-diepoxy octane and 17.9 g of 2-ethyl-2-oxazoline. The reaction mixture was heated for 15 hours under nitrogen with constant stirring and the reaction temperature was maintained between 150–170 degrees C. The GLC analysis of the reaction solution showed the formation of 60% of the mixed bicyclic amide acetal-epoxy product (Formula III wherein R is tetramethylene, $R'$ is ethyl and $R''$ and $R'''$ are hydrogen). The purified product (18.8 g of 99% purity) was found to have a boiling point of 110–115 degrees C. at 0.1–0.15 mm of Hg.

EXAMPLE 2

The procedure of Example 1 was followed using 30.4 g of 1,4-butane diol diglycidyl ether and 14.9 g of the 2-ethyl-2-oxazoline. The reaction mixture was heated at 150–170 degrees C. for two hours during which time 52% of the mixed bicyclic amide acetal-epoxy product formed. The product was found to boil at 150–160 degrees C. at 0.15 mm of Hg and also was found to have the structure of Formula III in which R is $CH_2OC_4H_8OCH_2$, $R'$ is ethyl and $R''$ and $R'''$ are hydrogen.

EXAMPLE 3

The procedure of Example 1 was followed using 25 g of vinyl cyclohexene dioxide and 16 g of the oxazoline. After 24 hours of reaction at 150–160 degrees C. 62% of the product formed. The product was found to boil at 115–117 degrees C. at 0.5 mm of Hg as a colorless liquid and was found to have the structure of Formula III in which $R'$ is ethyl, R is

and $R''$ and $R'''$ are hydrogen.

EXAMPLE 4 The procedure of Example 1 was followed using 29 g of 1,2,7,8-diepoxy octane and 17.0 g of 2-methyl-2-oxazoline. The reaction mixture was heated at 140–165 degrees C. for 18 hours during which time 58% of the desired product formed. The product was found to boil at 108–112 degrees C. at 0.15 mm Hg as a colorless liquid and it was found to have the structure of Formula III in which R' is methyl, R is n-butylene and R" and R"' are hydrogen.

I claim:

1. The process for preparing a monomer which contains both bicyclic amide acetal and epoxy groups comprising reacting a compound of Formula I

I with A compound of Formula II

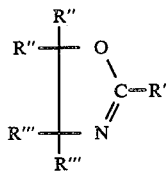

II wherein R represents a linear or cyclic alkylene group having from 1 to 30 carbon atoms, an arylene group having from 6 to 12 carbon atoms, an alkylene ether group having from 1 to 20 carbon atoms, or an arylene ether group having from 6 to 12 carbon atoms; R' represents an alkyl group having from 1 to 20 carbon atoms, an aryl group having from 6 to 12 carbon atoms L or an alkaryl group having from 7 to 20 carbon atoms, and R" and R"' independently represent hydrolgen, an alkyl group having from 1 to 10 carbon atoms or an aryl group having from 6 to 12 carbon atoms.

2. The process of claim 1 wherein the equivalent ratio of epoxy groups to oxazoline groups is in the range of from 5:1 to 1:1 and the reaction temperature is in the range of from 120°–200° C.

3. The process of claim 1 wherein the equivalent ratio of epoxy groups to oxazoline groups is in the range of from 2.5:1 to 1.5:1 and the reaction temperature is in the range of from 140°–170° C.

4. The process of claim 3 wherein there is also included an alkali or alkaline earth metal salt catalyst.

5. The process of claim 3 wherein the compound of Formula I is 1,2,7,8-diepoxy octane and the compound of Formula II is 2-ethyl-2-oxazoline.

6. The process of claim 3 wherein the compound of Formula I is 1,4-butane diol diglycidyl ether and the compound of Formula II is 2-ethyl-2-oxazoline.

7. The process of claim 3 wherein the compound of Formula I is vinyl cyclohexene dioxide and the compound of Formula II is 2-ethyl-2-oxazoline.

8. The monomer produced by the process of claim 1.

9. The monomer produced by the process of claim 1 wherein the equivalent ratio of epoxy groups to oxazoline groups is in the range of from 5:1 to 1:1 and the reaction temperature is in the range of from 120°–200° C.

10. The monomer produced by the process of claim 1 wherein the equivalent ratio of epoxy groups to oxazoline groups is in the range of from 2.5:1 to 1.5:1 and the reaction temperature is in the range of from 140°–170° C.

11. The monomer of claim 10 wherein the compound of Formula II is 2-ethyl-2-oxazoline.

12. The monomer of claim 11 wherein the compound of Formula I is 1,2,7,8 -diepoxy octane.

13. The monomer of claim 11 wherein the compound of Formula II is 1,4-butane diol diglcidyl ether.

14. The monomer of claim 11 wherein the compound of Formula I is vinyl cyclohexene dioxide.

* * * * *